United States Patent [19]
Weiner et al.

[11] Patent Number: 5,589,373
[45] Date of Patent: Dec. 31, 1996

[54] THERMOSTABLE ALKALINE METALLOPROTEASE PRODUCED BY A HYPHOMONAS AND PREPARATION THEREOF

[75] Inventors: Ronald M. Weiner, Adelphi; Juan Shi, College Park, both of Md.; Vernon E. Coyne, Lakeside, South Africa

[73] Assignee: University of Maryland at College Park, College Park, Md.

[21] Appl. No.: 478,808

[22] Filed: Jun. 7, 1995

Related U.S. Application Data

[63] Continuation of Ser. No. 104,847, Aug. 12, 1993, abandoned.

[51] Int. Cl.⁶ .................... C12N 9/52; C12N 15/57; C12N 15/70; C12N 1/22
[52] U.S. Cl. .................... 435/220; 435/68.1; 435/170; 435/172.3; 435/252.3; 435/252.33; 435/320.1; 536/23.2; 536/23.7; 935/14; 935/29; 935/73
[58] Field of Search .................... 435/69.1, 172.3, 435/252.3, 252.33, 220, 320.1, 68.1, 170; 536/23.2

[56] References Cited

U.S. PATENT DOCUMENTS

| | | | |
|---|---|---|---|
| Re. 30,602 | 5/1981 | TeNijenhuis | 252/99 |
| 2,549,465 | 4/1951 | Hoogerheide et al. | 195/96 |
| 3,669,844 | 6/1972 | Niwa et al. | 195/66 R |
| 3,674,643 | 7/1972 | Aunstrup et al. | 195/62 |
| 3,713,983 | 1/1973 | Yokotsuka et al. | 195/66 R |
| 3,723,250 | 3/1973 | Aunstrup et al. | 195/62 |
| 3,740,318 | 6/1973 | Churchill et al. | 195/65 |
| 3,827,938 | 8/1974 | Aunstrup et al. | 195/62 |
| 3,853,780 | 12/1974 | Mostow et al. | 252/132 |
| 3,858,854 | 1/1975 | Win et al. | 252/89 |
| 3,871,963 | 3/1975 | Tobe et al. | 195/62 |
| 3,960,665 | 6/1976 | Villadsen et al. | 195/66 R |
| 4,002,572 | 1/1977 | te Nijenhuis | 252/99 |
| 4,052,262 | 10/1977 | Horikoshi et al. | 195/66 R |
| 4,315,988 | 2/1982 | Miwa et al. | 435/221 |
| 4,390,629 | 6/1983 | Goldberg et al. | 435/220 |
| 4,442,214 | 4/1984 | Morgan et al. | 435/253 |
| 4,511,490 | 4/1985 | Stanislowski et al. | 252/174.12 |
| 4,610,800 | 9/1986 | Durham | 252/174.12 |
| 4,764,470 | 8/1988 | Durham et al. | 435/221 |
| 4,771,003 | 9/1988 | Stellwag et al. | 435/221 |
| 4,797,362 | 1/1989 | Takeuchi et al. | 435/221 |
| 4,865,983 | 9/1989 | Durham | 435/264 |
| 4,889,818 | 12/1989 | Gelfand et al. | 435/194 |
| 4,927,558 | 5/1990 | Aaslyng et al. | 252/174.12 |
| 4,965,197 | 10/1990 | Liebl et al. | 435/69.8 |
| 5,177,017 | 1/1993 | Lin et al. | 435/252.33 |

OTHER PUBLICATIONS

Ronald M. Weiner et al, "*Hyphomonas oceanitis* sp. nov., *Hyphomonas hirschiana* sp. nov., and *Hyphomonas jannaschiana* sp. nov." *Int'l Journal of Systematic Bacteriology*, Jul. 1985, vol. 35, No. 3, pp. 237–243.

R. L. Moore et al, "Genus *Hyphomonas* Pongratz 1957 nom. rev. emend., *Hyphomonas polymorpha* Pongratz 1957 nom. rev. emend., and *Hyphomonas neptunium* (Leifson 1964) comb. nov. emend. (*Hyphomicrobium neptunium*)", *Int'l Journal of Systematic Bacteriology*, Jan. 1984, vol. 34, No. 1, pp. 71–73.

Henryk M. Kalisz "Microbial Proteinases", *Biotechnology*,, vol. 36, 1988, pp. 1–65.

Shi, J., et al., 1989, Abstracts of the Annual Meeting of the American Society for Microbiology, 1989; 253, No. K–52.

Danaher, R. J., et al., 1990, Gene, 89(1): 129–133.

Farrell, D. H., et al., 1991, Biochemistry, 30(14): 3432–3436.

(List continued on next page.)

*Primary Examiner*—Robert A. Wax
*Assistant Examiner*—William W. Moore
*Attorney, Agent, or Firm*—Watson Cole Stevens Davis

[57] ABSTRACT

Novel thermostable alkaline metalloprotease produced by Hyphomonas which is stabile under conditions of elevated pH. Also included are a method for its production, and compositions containing the metalloprotease useful for degrading proteinaceous materials.

28 Claims, 5 Drawing Sheets

```
GATCC GAG ATC TGT CGT ATC GTA ATG GAC GGC CAT TGC GAG AAA
      Glu Ile Cys Arg Ile Val Met Asp Gly His Cys Glu Lys
      1             5                      10

CAG GGC GAT GCT GAG TGC CAC GAC GAC CAG CAG TCC GCT CGT
Gln Gly Asp Ala Glu Cys His Asp Asp Gln Gln Ser Ala Arg
            15                  20                  25

CCG GCG GAT CAG CGG ATA AAT CAG GAT GTA GAA CAG GTT GAT
Pro Ala Asp Gln Arg Ile Asn Gln Asp Val Glu Gln Val Asp
            30                  35                  40

GAC CAG TTC GAA GAA CAG GGT CCA GGC CGG AAC GTT TGC GGC
Asp Gln Phe Glu Glu Gln Gly Pro Gly Arg Asn Val Cys Gly
            45                  50                  50

ATA AAT GTA TTC GGA TCT CG.
Ile Asn Val Phe Gly Ser
            60
```

U.S. PATENT DOCUMENTS

Norquist, A., et al., 1990, Infection and Immunity, 58(11): 3731–3736.

Milton, D. L., et al., 1992, Journal of Bacteriology, 174(22): 7235–7244.

Bergquist, P. L., et al., 1987, in *Biotechnology and Genetic Engineering Reviews*, 5: 199–244.

McIntyre, M., et al., APMIS, 99(4): 316–320.

Jongeneel, C. V., et al., 1984, FEBS Letters, 242(2): 211–214.

Van Wart, H. E., et al., 1990, Proceedings of the National Academy of Sciences, U.S.A., 87: 5578–5582.

Fukusawa, S., et al., 1988, Agricultural and Biological Chemistry, 52(12): 3009–3014.

Black, W. J., et al., 1990, Journal of Bacteriology, 172(5): 2608–2613.

Kinoshita, T., et al., 1992, Proceedings of the National Academy of Sciences, U.S.A., 89: 4693–4697.

LeMoual, H., et al., 1991, The Journal of Biological Chemistry, 266(24): 15670–15674.

Figure 5.

```
GATCC GAG ATC TGT CGT ATC GTA ATG GAC GGC CAT TGC GAG AAA
      Glu Ile Cys Arg Ile Val Met Asp Gly His Cys Glu Lys
       1           5                   10

CAG GGC GAT GCT GAG TGC CAC GAC GAC CAG CAG TCC GCT CGT
Gln Gly Asp Ala Glu Cys His Asp Asp Gln Gln Ser Ala Arg
    15              20                  25

CCG GCG GAT CAG CGG ATA AAT CAG GAT GTA GAA CAG GTT GAT
Pro Ala Asp Gln Arg Ile Asn Gln Asp Val Glu Gln Val Asp
        30              35                  40

GAC CAG TTC GAA GAA CAG GGT CCA GGC CGG AAC GTT TGC GGC
Asp Gln Phe Glu Glu Gln Gly Pro Gly Arg Asn Val Cys Gly
            45              50                  50

ATA AAT GTA TTC GGA TCT CG.
Ile Asn Val Phe Gly Ser
            60
```

THERMOSTABLE ALKALINE METALLOPROTEASE PRODUCED BY A HYPHOMONAS AND PREPARATION THEREOF

This application is a continuation of application Ser. No. 08/104,847, filed Aug. 12, 1993 now abandoned.

FIELD OF THE INVENTION

The present invention relates to novel alkaline proteases, particularly novel extracellular alkaline metalloproteases which have excellent stability. Further, the present invention relates to: 1) at least one thermostable alkaline metalloprotease which is produced by novel microorganisms which belong to the genus Hyphomonas; 2) a method of preparing metalloprotease which functions as a proteolytic agent with a high degree of stability under conditions of elevated temperature and/or pH, comprising culturing the above microorganisms under conditions which induce the synthesis of the metalloprotease, and recovering alkaline metalloprotease from the culture; and 3) compositions for the degradation of proteinaceous materials including at least one of the above alkaline proteases.

BACKGROUND OF THE INVENTION

Proteases (or proteinases) are a subclass of hydrolases (one of the six classes of enzymes designated by the International Union of Biochemistry). The proteases form a highly complex group of enzymes which vary enormously in their physical, chemical and catalytic properties. However, all hydrolyze the peptide bonds between amino acids comprising the structural units of proteins. Thus, the proteolytic enzymes, effective intra- or extracellularly, play an important role in the metabolic and regulatory processes of animal and plant cells, as well as in prokaryotic and eucaryotic microorganisms.

Until about 15 years ago proteases were regarded as degradative enzymes which could only catalyze the total hydrolysis of proteins. However, recent advances in assay techniques, such as the use of more selective substrates, have demonstrated that proteolytic enzymes carry out highly specific and selective modifications of proteins by limited hydrolysis. Extracellular proteases (or exoproteases) are involved primarily in protein turnover, while intracellular enzymes also play a key role in the regulation of metabolic processes and the balance between protein synthesis and degradation.

Protein turnover eliminates abnormal proteins and is essential for the adaptation of cells to new environmental conditions. It is a continual process in all living cells. The cell utilizes proteases to break down polypeptides into their primary components when those polypeptides have no further value to the cell. Thus, a pool of amino acids are provided as precursors for the synthesis of essential proteins and a nitrogen source for nucleotide biosynthesis. The process is similar in all organisms, with different rates of turnover for individual proteins and subcellular fractions.

A number of mechanisms operate to control proteolysis. These include, for example, modulation of substrate proteins by covalent interconversion, change in hydrophobicity and interaction with various molecules, thereby affecting the susceptibility of the molecules to proteolysis. Protease activity is also controlled by nutritional conditions and catabolite repression. For example, in both microbial and mammalian tissues, protease activity has been shown to increase when the organism is placed under conditions of nutrient starvation. Thus, when the cell is starved, proteins serving newly required functions in the cell can be synthesized with little net change in protein content. In contrast, nutrients such as glucose have been shown to repress proteolytic activity in yeasts, Bacilli, *Escherichia coli* and other microorganisms.

Extracellular proteases usually have wide substrate specificities and can degrade most non-structural proteins, such as albumin, casein, insulin or hemoglobin. For example, many marine bacteria produce extracellular proteases in order to utilize proteinaceous macromolecules which accumulate on surfaces in the marine environment. Many pathogenic microorganisms secrete proteases, some of which are involved in the infection process. Several microbial species release specific proteases, including the collagenases, the elastases and the keratinases, which can hydrolyze structural and connective tissue proteins which are resistant to attack by most proteases.

Proteases are classified by their catalytic mechanism into four groups. These include: 1) serine proteases, 2) cysteine proteases, 3) aspartic proteases and 4) metallo-proteases. Characteristically, the enzymes of the metalloprotease category have an optimal pH between 5 and 9 and are sensitive to metal-chelating reagents, such as ethylenediaminetetraacetic acid (EDTA), but are unaffected by serine proteinase inhibitors or sulfhydryl agents. However, many of the EDTA-inhibited enzymes can be reactivated by the addition of ions, such as zinc, calcium, or cobalt.

Metalloproteases are widespread, although only a few have been reported in fungi. Most metalloproteases can be divided into three groups: acid, neutral or alkaline proteases. Characteristically, bacterial metalloproteases are zinc-containing enzymes, with one atom of zinc per molecule of enzyme. The zinc atom is essential for enzyme activity.

Moreover, calcium ions have been shown to stabilize the protein structure of the zinc-containing metalloproteases. However, the amount of calcium in a metalloprotease varies from four atoms per molecule for the *Bacillus thermoproteolyticus* thermolysin to less than 0.2 atoms per molecule for the *Aeromonas proteolytica* enzyme. The four calcium ions associated with thermolysin permit the enzyme to withstand increased temperature via a cooperative mechanism, while removal of $Ca^{2+}$ ions from the native enzyme results in an irreversible loss of catalytic activity at temperatures below 50° C., and irreversible structural changes at temperatures above 50° C.

In contrast, although the exoprotease produced by *Bacillus amyloliquefaciens* has properties similar to thermolysin, the enzyme molecule contains only two calcium ions and is considerably less heat stable. Thus, the ability of an alkaline metalloprotease to withstand high temperatures appears to be a function of the calcium ions associated with the enzyme.

The thermostable proteases currently in industrial use belong primarily to either the neutral metalloprotease or the alkaline serine groups. The neutral metalloproteases include thermolysin, which is stable up to 80° C. Proteases of this type are exemplified by cultures of *Thermus aquaticus*, such as taught by U.S. Pat. Nos. 4,889,818 and 4,442,214. However, neutral metalloproteases are inactivated by alkaline conditions, and have poor stability to oxidizing agents.

Alkaline serine proteases include the subtilisins, which have an optimal temperature of 60° C. Most commercially available alkaline proteases are produced by microorganisms belonging to the Bacillus and *Aspergillus genera*, although some are produced by Streptomyces, Arthrobacter, and Fusarium. Enzymes produced by cultivation of the genus Bacillus constitute the majority of proteolytic enzymes in present use, such as those described in U.S. Pat. Nos. 4,797,362, 4,771,003, and 3,871,963. Further, numerous other Bacillus-produced proteases are used in detergent washing compositions, such as those described in U.S. Pat. Nos. 4,764,470, 4,052,262, 4,002,572, and 3,827,938.

Bacillus alkaline proteases have broad specificity and certain species exhibit activity at elevated levels of alkalinity. Disadvantageously however, Bacillus alkaline proteases have less than desirable stability to oxidizing agents, such as hypochlorite or hydrogen peroxide, sensitivity to diisopropylphosphofluoridate and phenylmethylsulfonyl fluoride, and are completely unstable in chlorine bleaches. Furthermore, Bacillus culture results in the production of heat-resistant endospores, antibiotics and undesirable enzymes, in addition to the production of proteases.

In contrast, members of the Aspergillus species are non-pathogenic and non-toxic. However, mutants of the organisms are rather unstable. Thus, strain improvement is essentially rendered unfeasible.

Certain other bacteria are known to produce alkaline exoproteases which are characterized by stability over limited pH and temperature ranges, although each such protease is readily distinguished physically and biochemically from the protease produced by the present process. Alkaline proteases include those which are produced, for example, in accordance with U.S. Pat. Nos. 4,965,197, 4,865,983, and 4,390,629.

It is evident that there is a long-felt need in the art for thermostable proteolytic enzymes in industry and medicine. For example, until the present invention, the art has been unable to fulfill the need for thermostable alkaline exoproteases which can be used in preparing laundry detergents or in formulating animal feed, as catalysts in the drug and chemical industry, as reagents for converting starch to sugars, for destroying waste products or converting waste protein to useful alternative chemicals, for tanning, for generating peptides from cloned precursors, and in the dissolution of necrotic tissue or blood clots, and the like. Additional uses of proteolytic enzymes will undoubtedly be found.

In view of the foregoing, it is evident that although numerous proteases are known, that the prior art has not produced proteases which completely satisfy the need in the art for reliable, thermostable alkaline exoproteases. Accordingly, the identification and characterization of at least one novel thermostable alkaline exoprotease which is highly active on proteinaceous material at both high pH and elevated temperatures, as well as related methods of preparation and use, would significantly advance the art. The present invention satisfies this need and provides related advantages in the art.

SUMMARY AND OBJECTS OF THE INVENTION

In accordance with the present invention, at least one exoprotease produced by the marine bacterium, *Hyphomonas jannaschiana*, is an alkaline metalloprotease which has been determined to be unexpectedly and advantageously thermostable. Moreover, *H. jannaschiana* alkaline metalloprotease has been characterized and shown to be resistant to surprisingly high concentrations of chelating agents, such as EDTA, which are known to have broad substrate specificity. The amino acid sequence of thermostable alkaline metalloprotease has been determined, including definition of the active region.

Furthermore, in accordance with the present invention, a gene coding for thermostable alkaline metalloprotease has been identified, isolated, cloned and expressed in gram-negative microorganisms. The expression products in the host have been identified as active, functional, alkaline metalloprotease enzymes.

Accordingly, it is a primary object of the invention to provide substantially purified thermostable exoenzyme which is advantageously highly active on proteinaceous material.

It is also an object of the present invention to provide substantially purified thermostable proteolytic exoenzyme which advantageously exhibits a high degree of stability under alkaline conditions.

It is a particular object of this invention to provide such a thermostable alkaline exoprotease from the marine bacterium, *Hyphomonas jannaschiana*.

It is also a particular object of this invention to characterize thermostable alkaline metalloprotease which is synthesized by *Hyphomonas jannaschiana*, and further to define the amino acid sequence.

It is yet another object of this invention to provide a process for the preparation of a substantially purified novel alkaline metalloprotease from a culture of the marine bacterium, *Hyphomonas jannaschiana*.

It is a further primary object of this invention to isolate a gene coding for thermostable alkaline metalloprotease from the genome of the bacterium *Hyphomonas jannaschiana*.

It is an additional object of this invention to characterize an isolated gene coding for thermostable alkaline metalloprotease, and further to provide the nucleotide sequence of said gene.

It is also an object of this invention to manipulate an isolated gene coding for thermostable alkaline metalloprotease, utilizing recombinant technology, to insert the isolated gene into a gram-negative host, such as *E. coli*, by which the novel alkaline metalloprotease gene is expressed.

Still another object of this invention is to provide a gene coding for thermostable alkaline metalloprotease in a form which may be readily manipulated for further study and development. By inserting a gene in a well-characterized host, such as *E. coli*, the desired genetic manipulations will be greatly facilitated. For example, an isolated exoprotease gene can be associated with more powerful promoters, altered by site-directed mutagenesis, and the like.

It is an additional object of this invention to provide a process for the preparation of thermostable alkaline metalloprotease from a microbial expression and secretion system, in particular for the production of the mature enzyme(s).

It is also an object of this invention to provide a composition comprising thermostable alkaline metalloprotease for use in applications which require a composition which is highly active on proteinaceous material at high pH and elevated temperatures, and which has a high degree of stability under alkaline conditions.

Briefly, the present invention relates to a substantially purified thermostable alkaline metalloprotease having the following properties:

a) activity: denatures protein in highly alkaline conditions;

b) optimal pH: approximately 9.5 at a reaction temperature of about 60° to 65° C.;

c) pH range for stability: pH 6.5 to 13.0 at a temperature of 37° C.;

d) optimal temperature: 45° C. when reacted at pH 9;

e) thermal stability: at least 60% of the activity remains after incubation at pH 9 and 75° C. for 30 minutes, and at least 41% of the activity remains after boiling at 100° C. for 5 minutes;

f) effect of inhibitors: activity was inhibited by 5 mM o-phenanthroline and 80 mM ethylene glycol bis(beta-amino-ethylether)N,N,N',N'-tetraacetic acid (EGTA) and by 100 mM EDTA at concentrations greater than $10^{-2}$M; activity was not affected by 60 mM phenylmethyl sulfonamide fluoride (PMSF), 10 mM p-chloromercuribenzoic acid (pCMB) or thiol protease inhibitor E64; activity was abolished in the presence of mercaptoethanol;

g) effect of metal ions: active site contains a zinc ion and activity which has been inhibited by 5 mM o-phenanthroline is restored by the addition of $Zn^{2+}$; activity requires a calcium ion and activity which has been inhibited by 80 mM EGTA is restored by the addition of $Ca^{2+}$;

h) molecular weight: approximately 80,000 daltons;

i) isoelectric point: pI 4.8.

Additional objects, advantages and novel features of the invention will be set forth in part in the description which follows, and in part will become apparent to those skilled in the art on examination of the following detailed description of the preferred embodiments of the invention, or may be learned by practice of the invention.

BRIEF DESCRIPTION OF THE DRAWINGS

FIG. 5 shows a nucleotide sequence (SEQ ID NO:1) of the gene coding for thermostable alkaline metalloprotease produced by *H. jannaschiana* VP3, and the corresponding amino acid sequence region (SEQ ID NO:2).

DESCRIPTION OF THE PREFERRED EMBODIMENTS OF THE INVENTION

Figure 1:
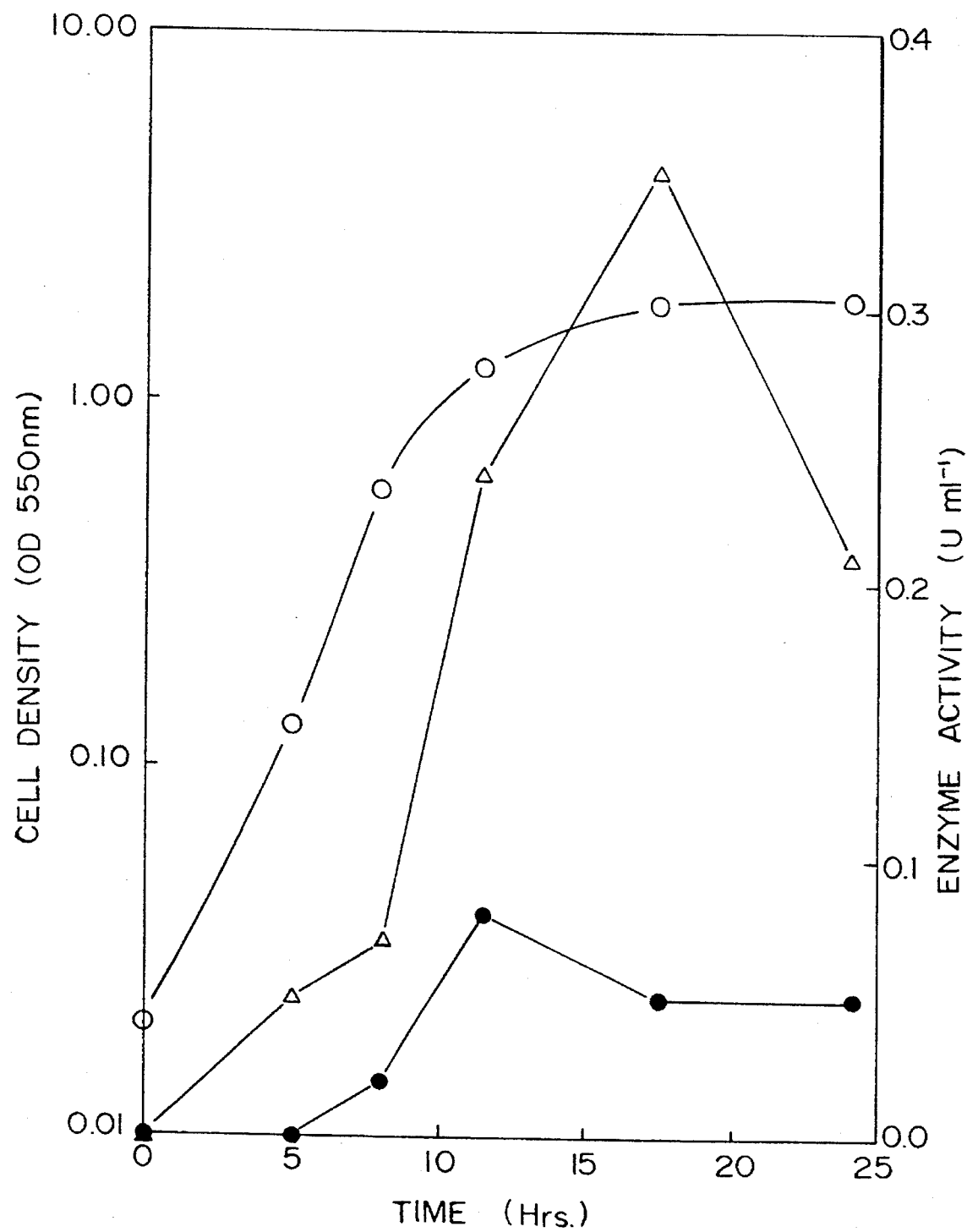
FIG. 1 is a line graph showing the exoprotease production in *H. jannaschiana* VP3.

The present invention relates to the production of at least one novel exoprotease, which is characterized by a high degree of thermal stability and stability under alkaline conditions. The enzyme can be produced by cultivating a bacterium of the species *Hyphomonas jannaschiana* in a fermentation medium, maintaining the cells at a stationary growth phase under inducing conditions in the medium, and recovering the protease(s) therefrom. As will be disclosed in greater detail below, exoprotease produce by *H. jannaschiana* is characterized by the following properties: stability under highly alkaline conditions, stability at high temperatures, stability at high temperatures under highly alkaline conditions, activity over a broad pH range, and activity at elevated temperatures.

The species which produces a protease of this invention, *Hyphomonas jannaschiana*, was initially isolated from the biofilm on a mussel shell and characterized as aerobic, Gram-negative, non-photosynthetic and budding bacteria. Strain VP3 was among the four strains which were initially isolated in 1979 from shellfish beds near hydrothermal vents in the vicinity of the Galapagos Islands as described by Jannasch et al., *Appl. Environ. Microbiol.* 35:567–594, 1981. The strains were classified as members of the novel species *Hyphomonas jannaschiana* by Weiner et al., *Int. J. Syst. Bacteriol.* 35:237–243, 1985, in a report based on the results of morphological, nutritional, biochemical, and serological evaluations of each strain. The protease producing species can be distinguished upon selection based on the characteri-zation presented in *Int. J. Syst. Bacteriol.*, supra, which is incorporated herein by reference.

*H. jannaschiana* is a prominent surface colonizing species which utilizes amino acids as a source of carbon and energy. The bacteria exhibit extracellular protease activity during the late-logarithmic and stationary phases of cell growth. Advantageously, *H. jannaschiana* is non-pathogenic and synthesizes no undesirable endospores, antibiotics or other exoenzymes.

Accordingly, the process of the present invention for the production of a thermostable alkaline proteolytic exoenzyme comprises fermenting a culture of the organism *Hyphomonas jannaschiana* in an aqueous nutrient fermentation medium under conditions which induce the synthesis and export of the proteolytic enzyme, and recovering same from the fermentation broth.

In the alternative, purified enzymes may be produced for industrial purposes by using genetic engineering to manipulate the gene coding for thermostable alkaline protease into other organisms from which it may be expressed. Recombinant techniques are important for both laboratory development and industrial production of the enzyme. Thus, genetic engineering provides an alternative method of large scale protease production while avoiding any factors which could be associated with the production of an enzyme in its natural environment.

Unless defined otherwise, all technical and scientific terms used herein have the meanings which are commonly understood by one of ordinary skill in the art to which this invention belongs. Moreover, unless mentioned otherwise, the techniques employed herein are standard methodologies well known to one of ordinary skill in the art, and all chemicals, reagents and the like are of analytical grade and obtained from commercial sources. Although any methods and materials similar or equivalent to those described herein can be used in the practice or testing of the present invention, the preferred methods and materials are now described.

For the purposes of this invention, the preferred enzyme is meant to include one or more substances which enzymatically hydrolyze the peptide bonds between amino acids comprising the structural units of proteins by a process known as proteolysis. Thus, the preferred enzyme is a "protease", also referred to as a "proteinase". Specifically, the preferred protease of the present invention functions as a proteolytic agent with a high degree of stability under conditions of elevated temperature and/or pH.

In particular, the protease of the present invention is preferably secreted from the cell into the surrounding medium, and therefore is termed an "exoprotease". More preferably, the exoprotease of the present invention is a "metallo-protease", which may be identified by sensitivity to certain metal-chelating reagents, such as o-phenanthroline, ethylene glycol bis(beta-amino-ethylether)N,N, N',N'-tetraacetic acid (EGTA) and ethylenediaminetetra-acetic acid (EDTA), but which is unaffected by specific serine proteinase inhibitors or sulfhydryl agents.

The protease-producing bacteria of the present invention denote bacteria of the genus Hyphomonas which will synthesize and export thermostable alkaline metalloprotease into the fermentation culture broth when aerobically cultivated under inducing conditions. In particular, the cultivation in accordance with this invention is usually carried out in a liquid medium.

Methods of cultivation include fermentation conditions of the surface (semisolid) or of the submerged type over relatively broad pH and temperature ranges. Extracellular enzymes are generally produced by batch processes which last up to 150 hours, although continuous systems are also known.

Most fermentation processes have high oxygen demand. The fermentation cultivation is conducted aerobically, for example, with shaking (e.g., 100–150 rpm), stirring, aerated agitation or blowing humidified air through the media. Typically, aeration is accomplished by mechanical agitation or air spargers.

For cultivating the present strains, it is possible to use any fermentation media, solid or liquid, which is suitable for conventional cultivation of microorganisms and which can be utilized by the present strains. Fermentation media, also referred to as culture media, are available commercially or may be prepared by formulas known in the art, containing an alkaline buffer as well as the assimilable sources of the components necessary for the microorganisms to grow, such as a carbon source, a nitrogen source, an inorganic salt, and the like.

A variety of growth media can be used for cultivating *Hyphomonas jannaschiana*. Preferably, the bacteria are grown aerobically on commercially available media, for example, Difco Marine Broth 2216 (Difco Laboratories, Detroit, Mich.), or on marine medium prepared in accordance with Zobell, *J. Mar. Res.* 4:42–75 (1941).

Sources of carbon which are suitable for use in the fermentation medium include carbohydrate sources such as ground yellow dent corn, white corn, potatoes, starch, sucrose, mannose, fructose, mannitol, maltose, cellobiose, dextrin, corn syrup, molasses, ground oats, barley, wheat, and the like.

The nitrogen source can be in the organic or inorganic form. Examples of nitrogen sources include peptone, soybean flour, soybean casein, defatted soybean flour, corn steep liquor, oat, barley or wheat-bran extracts, dried yeast, yeast extract, ammonia, urea, and the like; or suitable ammonium salts, such as ammonium chloride and ammonium sulfate, and the like.

Examples of inorganic mineral salts include, for example, chlorides or sulfates of the divalent ions $Ca^{2+}$, $Mg^{2+}$ and $Mn^{2+}$, e.g., calcium chloride, magnesium sulfate, or may include potassium phosphate, dipotassium phosphate, and the like. The metal ions may be present singly or in combination in the culture medium at a suitable final concentration of 1 mM to 1.2M, preferably 5 to 1000 mM, and especially approximately 10 to 700 mM.

The cultivation temperature and the pH of the culture medium vary depending upon the bacterial strain used. The fermentation media is maintained at a pH of about 6.0 to about 9.5, and preferably from about 7.0 to about 8.5, and most preferably at about 7.6. Examples of alkaline buffers include sodium carbonate, potassium carbonate, sodium bicarbonate, sodium phosphate, sodium tetraborate, and the like.

The fermentation temperature is suitably in the range of about 20° C. to about 40° C., preferably about 37° C. The NaCl concentration for optimum growth ranges from about 3.0 to about 7.5%, but is preferably approximately 3.5%.

Optionally, various other organic or inorganic substances may be added as necessary for the growth of the microorganisms or the production of the enzymes. For example, a rich medium may include partially hydrolyzed animal or plant protein, rich in amino acids, short peptides, and lipids; or yeast extract, rich in vitamins and enzymatic cofactors, nucleic acid precursors, and amino acids; or selective factors, such as antibiotics, including streptomycin, penicillin, or tetracycline. In particular, the induction of bacterial exoprotease production usually requires the presence of large peptides or protein in the fermentation media.

The media components are sterilized in a conventional manner and inoculated with the desired strain of microorganism. In particular, the sterilized selected media is inoculated with a member of the genus Hyphomonas, specifically with a member of the species *Hyphomonas jannaschiana*, more specifically with a member of strain VP3.

A productive fermentation typically is in the range of 20–50 hours, and preferably about 30 hours. Optimally, exoenzymes are detectable in the culture supernatant after about 17 hours of fermentation.

In the alternative, the cells may be harvested at the early stationary growth phase and resuspended in a reduced volume of media to induce production of exoprotease in the culture fluid. If cell culture conditions are optimal, the cells will grow and reproduce near their theoretical maximum. Cells dividing rapidly in balance growth are said to be in an exponential (or log) phase of growth. However, as cell density increases exponentially, cell growth and division will eventually essentially stop, even if sufficient growth nutrients are present—a phenomenon referred to as density-dependent inhibition of cell division. Cells have then reached stationary growth phase and viable cell population stops increasing although protease may continue to accumulate.

Typically, in the present invention, early stationary growth phase cells are resuspended in fresh growth media at a 10-fold greater cell density. The amount of necessary growth nutrients are limited by increasing the cell density, and as a result the cells are maintained in the stationary growth phase for maximum exoprotease production.

Various factors can affect the synthesis of exoprotease by the cell. A constitutive enzyme is produced by a cell regardless of the presence of its substrate; in contrast, many proteins are produced by bacterial strains only in the presence of a regulatory stimulus. By making the appropriate regulator available, the bacterium manufactures the enzymes needed for the uptake and metabolism of the stimulator that it finds in the medium. The specific response is referred to as "enzyme induction", and the synthesis of the protein is said to be "induced" from the cell by the addition of a substrate for the enzyme.

For example, the cellular synthesis of an exoprotease may be induced by the addition of protein and large polypeptides to the fermentation media, although the secretion of the exoenzyme occurs constitutively. In addition, exoprotease synthesis may be negatively regulated by end-product inhibition, whereby enzyme production ceases in the presence of certain amino acids. In particular, in accordance with the present invention, the production of *H. jannaschiana* exoprotease may be subjected to induction by the addition of protein and large polypeptides to the fermentation media, and to end-product repression by the addition of various amino acids.

Following maximum synthesis and export of the exoprotease into the fermentation broth, typically for a period of about 2–6 hours, the cells are removed from the spent media by any recognized method, including for example, centrifugation or filtration. Typically, the cells and residual solid material are removed by centrifugation and the supernatant is filtered, usually by a 0.22 μm filter.

Separation may be aided by pretreating the suspension with a coagulating or flocculating agent. Efficient flocculation may utilize synthetic polyelectrolytes, such as polyamines. In some cases, filter aids, such as diatomaceous earth, may be added before filtration.

Frequently, the separation process is aided by permitting the spent media to settle so that the colloids aggregate before separation. However, this step may be limited by cost and contamination constraints. In large or industrial scale preparations, the separation process may be performed on vacuum drum or leaf filters or in high speed centrifuges.

Crude or purified alkaline exoprotease is collected in the form of a precipitate or concentrated liquid from the aqueous cell-free protease suspension by one or more processes recognized in the art. The processes may include, for example, conventional salting out by the addition of an inorganic salt, precipitation by the addition of ion-exchange resins or an organic solvent, multistage vacuum evaporation, ultrafiltration, isoelectric point precipitation, condensation under reduced pressure, or gel filtration.

Suitable inorganic salt precipitating agents may include, for example, ammonium sulfate, calcium sulfate, calcium phosphate, or sodium sulfate. Suitable organic solvent separating agents may include, for example, isopropanol or ethanol.

Ion exchange resins provide a solid solution of an active electrolyte in a highly stable insoluble matrix. Suitable ion exchange resins may include cation exchange resins which include acidic functional groups, such as sulfonic acid or carboxylic acid, or anion exchange resins which include alkaline functional components, such as quaternary ammonium or amino groups.

The ultrafiltration process, in many cases, may prove to be advantageous since it is inexpensive. It enables the removal of substances having molecular weights less than 10 kD and can be performed at low temperatures (about 5° C.) which minimizes the loss of activity and the risk of contamination. The enzyme solution may be further clarified by a polishing filtration method, or the remaining microorganisms may be removed by germ filtration on cellulose-containing filter pads.

The filtrate may be subsequently mixed with optional stabilizers and/or preservatives. Stabilizers, such as calcium salts, proteins, starch hydrolysates, and sugar alcohols, are used to increase the storage stability of the enzyme preparation. Preservatives may include, for example, sodium chloride (18–20%), or benzoate, parabene, or sorbate.

Liquid enzyme preparations are often preferred to their solid counterparts if they are cheaper to produce, safer and more convenient to apply. However, solid preparations are often desirable for specific purposes. Solid enzymes are prepared either by direct spray-drying of the enzyme solution or by precipitation. Increased purity is obtained when the solid enzyme is precipitated with solvents, such as acetone or ethanol, or organic salts, such as ammonium or sodium sulfate. The resulting precipitate is removed by filtration and dried. The purification process may occasionally include a step which removes an undesirable side effect. For example, in the production of microbial rennet by *M. miehei*, it has been shown to be desirable to remove lipase during the purification process.

The dried enzyme preparations often form large lumps which are ground to a fine powder in a mill and the activity standardized by the addition of inert compounds, such as salt or lactose. Problems in handling dusty powders, especially in the detergent industry, have led to the development of dust-free granulates which also have improved storage stability.

Enzymes for the detergent industry may be granulated by embedding enzyme into spheres of a waxy material consisting of a nonionic surfactant by means of a spray-cooling or prilling process. In the alternative, enzyme may be mixed with a filler, a binder, and water, then extruded, and subsequently formed into spheres in a so-called marumeriser. The spheres are then dried and coated with a layer of inert material, such as wax or a soluble cellulose derivative.

The optimal activity of thermostable alkaline protease of the present invention occurs at a pH of about 9–11, but preferably about 10, at an optimal working temperature of about 37°–55° C., but preferably about 45° C. However, thermostable alkaline exoprotease activity, measured by an azocasein assay, was found to decrease by only about 40% following incubation at 75° C. for 30 minutes; and even boiling the preparation for 5 minutes did not destroy the proteolytic activity. The heat stability of the protease may also be influenced by the addition of metal salts, such as $CaCl_2$, $MnCl_2$, $MgSO_4$, $CoCl_2$, and the like.

Alkaline metalloproteases are slightly larger than the other metalloproteases, having an average molecular weight of approximately 55,000 daltons. In particular, *H. jannaschiana* synthesizes thermostable alkaline metalloprotease which has an approximate molecular weight of 80,000 daltons, and which is exported from the cell via a signal peptidase.

Exoenzymes are generally synthesized as large, inactive precursor proteins which must be translocated across or integrated into cellular membranes. The precursors typically contain a short amino terminal extension of 15–40 amino acid residues, called a "signal peptide". Upon export, the leader sequence is removed by the action of a signal peptidase.

Assays have shown that in certain species the signal peptide of particular exoenzymes is susceptible to inhibition by the addition of quinacrine. As a result, the amount of active extracellular enzyme is significantly reduced. Our data suggests that *H. jannaschiana* alkaline metalloprotease is exported via a similar mechanism, whereby inactive, cytoplasmic proenzyme is processed by a signal peptidase, resulting in "active" or "functional" extracellular protease. Activity can be determined by the effect of the exoprotease in an azocasein assay.

Also contemplated for use herein are mutants and hybrids of the foregoing protease which substantially retain the performance characteristics thereof, i.e., which satisfy the assays for optimal proteolytic activity as a function of pH. Moreover, such mutants and/or hybrids must exhibit alkaline stability at elevated temperatures. As used herein, the term "mutant" refers to protease in which a change is present in the amino acid sequence as compared with wild type or parent enzymes. "Hybrid" refers to protease which combines the amino acid sequence from two or more parent enzymes and exhibit characteristics common to both.

In addition to obtaining thermostable alkaline exoprotease by cultivation of *Hyphomonas jannaschiana* cells, inducing the synthesis and export of the enzyme, and isolating and purifying the desired protein, protease can be expressed by recombinant DNA technology.

Moreover, modifications can be made to the primary structure of a protease by deletion, addition, or alteration of the amino acids incorporated into the sequence during translation, without destroying the thermostable alkaline proteolytic activity. Such substitutions or other alterations result in proteins having an amino acid sequence encoded by a DNA which falls within the contemplated scope of the present invention.

As detailed below, there are a number of methods and variables to consider in the construction of a system for expression of a protein. The first consideration is the determination of the protein to be expressed and the isolation of a DNA gene sequence which encodes some or all of the mature (used here to include all muteins) protease, or a fusion of protease to an additional sequence that does not destroy its original proteolytic activity or to an additional sequence which is cleavable under controlled conditions (such as treatment with peptidase) to result in a proteolytically active protein.

The term "gene" or "gene sequence" as used herein refers to a DNA sequence that encodes a recoverable bioactive polypeptide or precursor. The polypeptide can be encoded by a full-length gene sequence or any portion of the coding sequence, so long as the enzymatic proteolytic activity is retained.

Accordingly, in the present invention, there is provided a DNA fragment which comprises a nucleotide sequence that encodes the aforementioned purified, functional thermostable alkaline metalloprotease. The DNA fragment of the present invention may comprise any nucleotide sequence, provided that, when the appropriate host cells are transformed with said DNA fragment by an appropriate method, that functional thermo-stable alkaline metalloprotease of the present invention is expressed in the thus transformed host cells.

The isolated DNA may be analyzed by restriction and/or recognized sequencing techniques, or more particularly, by commercially available methods and preparations. Preferably the DNA fragment comprises at least a nucleotide sequence (SEQ ID NO:1) as a part of the DNA nucleotide sequence:

GATCC GAG ATC TGT CGT ATC GTA ATG GAC GGC CAT TGC GAG AAA CAG GGC GAT GCT GAG TGC CAC GAC GAC CAG CAG TCC GCT CGT CCG GCG GAT CAG CGG ATA AAT CAG GAT GTA GAA CAG GTT GAT GAC CAG TTC GAA GAA CAG GGT CCA GGC CGG AAC GTT TGC GGC ATA AAT GTA TTC GGA TCT CG.

Also included within the scope of this invention are the functional equivalents of the herein-described DNA or nucleotide sequences. The degeneracy of the genetic code permits substitution of certain codons by other codons which specify the same amino acid and hence would give rise to the same protein. The DNA or nucleotide sequence can vary substantially since, with the exception of methionine and tryptophan, the known amino acids can be coded for by more than one codon. Thus, portions or all of the protease gene could be synthesized to give a DNA sequence significantly different from that shown in FIG. 5. The encoded amino acid sequence thereof would however, be preserved.

In addition, the DNA or nucleotide sequence may comprise a nucleotide sequence which results from the addition, deletion or substitution of at least one nucleotide to the 5'-end and/or the 3'-end of the DNA formula of FIG. 5, or a derivative thereof. Any nucleotide or polynucleotide may be used in this regard, provided that its addition, deletion or substitution does not alter the amino acid sequence of FIG. 5 which is encoded by the nucleotide sequence. For example, the present invention is intended to include a nucleotide sequence resulting from the addition of ATG as an initiation codon at the 5'-end of the inventive nucleotide sequence or its derivative, or from the addition of TTA, TAG or TGA as a termination codon at the 3'-end of the inventive nucleotide sequence or its derivative. Moreover, the DNA fragment of the present invention may, as necessary, have restriction endonuclease recognition sites on its 5'-end and/or 3'-end.

Such functional alterations of a given DNA or nucleotide sequence afford an opportunity to promote secretion and/or processing of heterologous proteins encoded for by foreign DNA sequences fused thereto. All variations of the nucleotide sequence of the protease gene and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified DNA molecule. Said two poly-peptides are functionally equivalent, as are the two DNA molecules which give rise to their production, even though the differences between said DNA molecules are not related to degeneracy of the genetic code.

Techniques for the preparation of structurally modified proteins are well known to those skilled in the art and may include exposure of a microorganism to radiation or chemicals and site-directed mutagenesis. However, mutagenesis by radiation or chemicals is essentially a random process and can require a tedious selection and screening to identify microorganisms which produce enzymes having the desired characteristics. Thus, a preferred structurally modified protease for the purposes of this invention is prepared by site directed mutagenesis. This procedure involves modification of the protease gene such that substitutions, deletions and/or insertions of at least one amino acid at a predetermined site are produced in the resultant protein, so long as the protein's proteolytic function remains essentially unchanged by the modification. Suitable techniques for site directed mutagenesis are well know to those skilled in the art.

Standard methods for the isolation of protein-coding sequences are known to those skilled in the art of genetic engineering. For example, the DNA fragment of the present invention may be obtained by chemical synthesis or by isolation from an appropriate chromosomal library or cDNA library.

A genetic sequence is suitable for expression in a host if it is uninterrupted by introns. The sequence is preferably in an excisable and recoverable form suitable for cloning into an appropriate vector.

In the alternative, chemical synthesis of the DNA fragment of the present invention may be chemically synthesized. For example, a DNA fragment with the nucleotide sequence which codes for the polypeptide of interest, thermostable alkaline metalloprotease may be designed and, if necessary, divided into appropriate smaller fragments. Then an oligomer which corresponds to the DNA fragment, or to each of the divided fragments, may be synthesized. Such synthetic oligonucleotides may be prepared, for example, by the triester method of Matteucci et al., *J. Am. Chem. Soc.* 103: 3185–3191 (1981) or by using an automated DNA synthesizer (e.g., model 380A by Applied Biosystems).

The term "oligonucleotide" or "oligomer", used interchangeable herein, is defined as a molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

If necessary, the 5'-ends of the oligomers may be phosphorylated using T4 polynucleotide kinase. Kinasing of single strands prior to annealing or for labeling may be achieved using an excess of the enzyme, e.g., approximately 10 units of polynucleotide kinase to 1 nM substrate in the presence of 50 mM Tris, pH 7.6, 10 mM $MgCl_2$, 5 mM DTT, and 1–2 mM ATP. If kinasing is for the labeling of probe, the ATP may contain high specific activity radioisotopes.

Then, the DNA oligomer may be subjected to annealing and ligation with T4 ligase or the like. For example, ligations may be performed in 1514 30 µl volumes under the following standard conditions and temperatures: 20 mM Tris-Cl, pH 7.5, 10 mM $MgCl_2$, 10 mM DTT, 33 µg/ml bovine serum albumen (BSA), 10–50 mM NaCl, and either 40 µM ATP, 0.01–0.02 units T4 DNA ligase at 0° C. (for "sticky end" ligation) or 1 mM ATP, 0.3–0.6 units T4 DNA ligase at 14° C. (for "blunt end" ligation). Intermolecular "sticky end" ligations are usually performed at 33–100 µg/ml total DNA concentrations (5–100 nM total end concentration). Intermolecular "blunt end" ligations (usually employing a 10–30 fold molar excess of linkers) are usually performed at 1 µM total ends concentration.

The synthesized DNA fragment may be used to probe an appropriate chromosomal or cDNA library by usual hybridization methods to obtain the fragment of the present invention. In the alternative, chemical synthesis is carried out in order to obtain DNA fragments having nucleotide sequences which correspond to N-terminal and C-terminal portions of the amino acid sequence of the polypeptide of interest, thermostable alkaline metalloprotease. Thus, the synthesized DNA fragments may be used as primers in a polymerase chain reaction (PCR) carried out essentially according to PCR *Protocols, A Guide to Methods and Applications*, edited by Michael, A. I. et al., Academic Press, 1990, utilizing the appropriate chromosomal or cDNA library to obtain the fragment of the present invention.

In particular, as described in the Examples of the present invention, a primer may be utilized with synthetic templates to determine the nucleotide sequence of the gene for *H. jannaschiana* alkaline metalloprotease utilizing recognized PCR techniques.

The term "primer" as used herein refers to an oligonucleotide which is capable of acting as a point to initiate synthesis when placed under conditions in which synthesis of a primer extension product which is complementary to a nucleic acid strand is initiated, i.e., in the presence of four different nucleotide triphosphates and thermostable enzyme in an appropriate buffer ("buffer" includes pH, ionic strength, cofactors, etc.) and at a suitable temperature.

The primer is preferably single-stranded for maximum efficiency in amplification, but may in the alternative be double-stranded. If double-stranded, the primer is first treated to separate its strands before being used to prepare extension products. The primer may also be an oligodeoxyribo-nucleotide.

The primer must be sufficiently long to prime the synthesis of extension products in the presence of the thermostable enzyme. The exact lengths of the primers will depend on many factors, including temperature, source of primer and method used. For example, depending on the complexity of the target sequence, the oligonucleotide primer typically contains 15–25 nucleotides, although it may contain more or fewer nucleotides. Short primer molecules generally require cooler temperatures to form sufficiently stable hybrid complexes with the template.

The primers herein are selected to be "substantially" complementary to the different strands of each specific sequence to be amplified. In other words, the primers must be sufficiently complementary to hybridize with their respective strands; however, the primer sequence need not reflect the exact sequence of the template. For example, a non-complemen-tary nucleotide fragment may be attached to the 5' end of the primer, with the remainder of the primer sequence being complementary to the strand.

Alternately, non-complementary bases or longer sequences can be interspersed into the primer, provided that the primer sequence is sufficiently complementary with the sequence of the strand to be amplified to hybridize therewith, and thereby form a template for synthesis of the extension product of the other primer. However, for detection purposes, particularly using labeled sequence-specific probes, the primers typically have exact complementarity to obtain the best results.

A chromosomal DNA or cDNA library, such as the library relied upon in the Examples of the present invention, may be prepared from appropriate cells according to recognized methods in the art (cf. *Molecular Cloning: A Laboratory Manual*, second edition, edited by Sambrook, Fritsch, & Maniatis, Cold Spring Harbor Laboratory, 1989). For example, a strategy for isolating DNA which encodes a desired proteins, such as that which encodes *Hyphomonas jannaschiana* protease, using the bacteriophage vector λgt11, may be as follows. A library can be constructed of EcoRI-flanked AluI fragments, generated by complete digestion of *Hyphomonas jannaschiana* DNA, inserted at the EcoRI site in the λgt11 phage (Young and Davis, *Proc. Natl. Acad. Sci. U.S.A.* 80:1194–1198 (1983)). Because the unique EcoRI site in this bacteriophage is located in the carboxy-terminus of the beta-galactosidase gene, inserted DNA (in the appropriate frame and orientation) is expressed as protein fused with beta-galactosidase under the control of the lactose operon promoter/operator.

Genomic expression libraries may be screened for hybridization using probes that recognize DNA segments which encode the $MW_{approx}$ 80,000 dalton exoprotease, or portions thereof, in order to identify phage that carry at least part of the DNA fragment. Approximately 20,000 recombinant phage are screened. In the primary screen, positive signals may be detected and one or more phages selected from the candidate plaques which failed to react with the screening agent. The selected recombinant phages containing the DNA fragment of interest may then be purified by any recognized method in the art, and cloned into an appropriate vector.

Preferably, the excised or recovered coding sequence is placed in operable linkage with suitable control sequences in a replicable expression vector.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet to be defined sequences. By comparison, eucaryotic cells are known to utilize promoters, polyadenylation signals, and enhancers.

"Operably linked" refers to juxtaposition of the components such that normal function can be performed. Thus, a coding sequence "operably linked" to a control sequence refers to a configuration wherein the coding sequence can be expressed under the control of the control sequence.

An system for "expression" refers to DNA sequences containing a desired coding sequence and one or more control sequences in operable linkage, so that a host transformed with these sequences is capable of producing the encoded protein. In order to effect transformation, the expression system may be included on a vector; however, the relevant DNA may also be integrated into the host chromosome.

Thus, the second consideration in the construction of an expression system is the selection of an appropriate vector, which may be used to transform a suitable host. Then, the transformed host may be cultured under favorable conditions to effect the production of recombinant protease. Optionally, protease is isolated from the medium or from the cells; or recovery and purification of the protein may not be necessary in some instances, where some impurities may be tolerated.

Each of the foregoing steps can be performed in a variety of ways. For example, the desired coding sequences may be obtained from genomic fragments and integrated directly into appropriate hosts. The constructions for expression vectors operable in a variety of hosts are made by using appropriate replicons and control sequences, as set forth below. Suitable restriction sites can, if not normally available, be added to the ends of the coding sequence to provide an excisable gene to insert into the vectors.

The construction of suitable vectors containing the desired coding and control sequences employs standard ligation and restriction techniques that are well understood in the art. For example, isolated plasmids, DNA sequences, or oligonucleotides may be cleaved, tailored, and religated into the form desired.

Site-specific DNA cleavage may be performed by treating the DNA with suitable restriction enzyme(s) under conditions that are generally understood in the art, and the particulars of which are specified by the manufacturer of the commercially available restriction enzymes. As used herein, the terms "restriction endonuclease(s)" and "restriction enzyme(s)" refer to a bacterial enzyme(s) which cuts double-stranded DNA at or near a specific nucleotide sequence.

In general, about 1 µg of the plasmid or specific DNA sequence is cleaved by one unit of restriction enzyme in about 20 µl of buffer solution. More particularly in the examples described herein, typically an excess of restriction enzyme is used to ensure complete digestion of the DNA substrate. Incubation times of about one hour to two hours at about 37° C. are effective, although variations can be tolerated.

After each incubation, protein may be removed by extraction with phenol/chloroform, which may be followed by ether extraction, and the nucleic acid may be recovered from the aqueous fractions by precipitation with ethanol. If desired, size separation of the cleaved fragments may be performed by polyacrylamide gel or agarose gel electrophoresis using standard techniques. A general description of size separations may be found in *Methods in Enzymology* (1980) 65:499–560.

Restriction-cleaved fragments may be blunt-ended by treatment with the large fragment of *E. coli* DNA polymerase I (Klenow) in the presence of the four deoxynucleotide triphosphates (dNTPs) using incubation times of about 15 to 25 minutes at 20° to 25° C. in 50 mM Tris, pH 7.6, 50 mM NaCl, 10 mM $MgCl_2$, 10 mM dithiothreitol (DTT) and 50–100 µM dNTPs. The Klenow fragment fills in at 5' sticky ends, but chews back protruding 3' single strands, even though the four dNTPs are present. If desired, selective repair can be performed by supplying the dNTP, or selected dNTPs, which are required by the specific sticky ends to be repaired. After treatment with Klenow, the mixture may be extracted with phenol/chloroform and ethanol precipitated. Additional treatment under appropriate conditions with S1 nuclease results in the hydrolysis of any single-stranded portion.

In vector construction employing "vector fragments", the vector fragment is commonly treated with bacterial alkaline phosphatase (BAP) in order to remove the 5' phosphate and prevent religation of the vector. Typically, BAP digestions are conducted at about pH 8 in approximately 150 mM Tris, in the presence of Na and Mg ions using about 1 unit of BAP per mg of vector at 60° C. for about one hour. In order to recover the nucleic acid fragments, the preparation may be extracted with phenol/chloroform and ethanol precipitated. Alternately, religation can be prevented in vectors that have been double digested by additional restriction enzyme digestion of the unwanted fragments.

For portions of vectors derived from cDNA or genomic DNA that require sequence modifications, site-specific primer-directed mutagenesis may be used. This technique is now standard in the art, and may be conducted using a synthetic oligonucleotide primer complementary to a single-stranded phage DNA to be modified except for limited mismatching, representing the desired mutation. Briefly, the synthetic oligonucleotide may be used as a primer to direct synthesis of a strand complementary to a phage, with the resulting double-stranded DNA then transformed into a phage-supporting host bacterium. Cultures of the transformed bacteria are plated in top agar, permitting plaque formation from single cells that harbor the phage.

Theoretically, 50% of the new plaques will contain the phage having, as a single strand, the mutated form; whereas, 50% will have the original sequence. The plaques may be transferred (lifted) to nitrocellulose filters and the "lifts" hybridized with kinased synthetic primer at a temperature that permits hybridization of an exact match, but at which the mismatches with the original strand are sufficient to prevent hybridization. Plaques that hybridize with the probe are then selected and cultured, following which the DNA may be recovered.

The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the polypeptide of interest, thermostable alkaline metalloprotease. Suitable hosts may often include eucaryotic microbes, such as yeast, e.g., including laboratory strains of *Saccharomyces cerevisiae*, although a number of other strains are commonly available. It is also, of course, possible to express genes encoding polypeptides in eucaryotic host cell cultures derived from multicellular organisms. Useful host cell lines may include murine myelomas N51, VERO and HeLa cells, COS cells, Chinese hamster ovary (CHO) cells and the like.

In addition, plant cells are also available as hosts, and control sequences compatible with plant cells are available, such as the nopaline synthase promoter and polyadenylation signal sequences. Moreover, expression systems employing insect cells, such as those which utilize the control systems provided by baculovirus vectors are recognized in the art.

Procaryotic hosts are, generally, the most efficient and convenient for the production of recombinant proteins and, therefore, are preferred for the expression of the protease. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC18, pUC19 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

More specifically, in accordance with the present invention, *E. coli* is typically transformed using derivatives of pBR322, a plasmid derived from an *E. coli* species as described by Bolivar et al., *Gene* 2:95 (1977). PBR322 contains the genes for ampicillin (Amp) and tetracycline (Tet) resistance, and thus provides additional markers that can be selectively retained or destroyed in constructing the desired vector.

Suitable plasmid, phage or virus vectors for the DNA fragment of the present invention may already contain the necessary procaryotic control sequences for the expression and secretion of the polypeptide of interest, thermostable alkaline metalloprotease. Procaryotic control sequences are defined herein to include promoters for transcription initiation, optionally with operator and ribosome binding site and/or signal peptide sequences and the like. In the alternative, nucleotide sequences necessary for the expression and secretion may be synthesized chemically and then inserted into an appropriate site of a selected plasmid, phage or virus vector together with the DNA fragment of interest in accordance with standard recognized insertion procedures (cf. *Molecular Cloning: A Laboratory Manual*, supra).

Commonly used promoters include, for example, the beta-lactamase (penicillinase) and lactose (lac) promoter systems (Chang et al., *Nature* 198:1056 (1977)), the tryptophan (trp) promoter system (Goeddel et al., *Nucl. Acids Res.* 8:4057 (1980)), the lambda-derived P L promoter (Shimatake et al., *Nature* 292:128 (1981)) and the like. However, any available promoter system compatible with procaryotes can be used.

Standard techniques are recognized by which the DNA molecule of interest may be introduced into the host organism in which it can replicate. Depending on the host cell recognized methods may be employed to permit the recombinant plasmid (transformation) or the recombinant bacteriophage (transfection) bearing the DNA of interest to penetrate into the host cell.

Suitable methods may include calcium chloride treatment, rubidium chloride or the like to transform procaryotes or other cells that contain substantial cell wall barriers, or calcium phosphate precipitation or the like to transform mammalian cells without cell walls. In the alternative, recombinant bacteriophage may be packaged into viable virus particles in vitro, then used to directly infect the susceptible host cells.

Following transformation, the host cells harboring the desired DNA fragment may be selected by any method recognized in the art. The selected transformants may then be cultured under conditions which induce the synthesis and production of the polypeptide of interest, specifically thermostable alkaline metalloprotease. Finally, protein may be recovered and/or purified from the transformant culture in accordance with standards methods, such as those heretofore disclosed with regard to the substantial purification of the native thermostable alkaline metalloprotease.

When cloning heterologous proteins for purification, it is often desirable to have the gene product hyperproduced and/or secreted by the host cells. The major advantages of secretion over intracellular accumulation of recombinant proteins are an increase in yield and the facilitation of product purification.

Secretion vectors are a specialized form of expression vectors and which are specifically designed for each cloning system. They must carry efficient transcriptional and translational start signals as well as sequences coding for the N-terminal portion (at least the signal peptide) of a secreted protein. Certain secretion vectors have been constructed and are recognized in the art as suitable for various microbial cloning hosts, including *E. coli*.

The efficiency of this system can be tested by in-frame fusions of foreign genes, such as the structural gene for *E. coli* beta-lactamase devoid of its own expression/secretion signals, to the signal sequence. Expression of the gene fusion can be regulated either by the native promoter of the chosen exoprotein gene or by a selected homologous exogenous bacterial promoter. Thus, the amount and integrity of foreign protein released to the growth medium upon transformation of *E. coli* with the gene fusion demonstrates the capacity of the selected host organism to produce and secrete the recombinant protein.

A particularly suitable vector for the present invention which uses the lac expression system is pUC19, which is available commercially, for example from Pharmacia P-L Biochemicals, Inc., Piscataway, N.J., from Promega, Madison, Wis., or from Bethesda Research Laboratories, Bethesda, Md. PUC19 is a small *E.coli* plasmid cloning vehicle described by Yanich-Perron et alo, Gene 33:103–119 (1985). The vector consists of the PvuII/EcoRI fragment of pBR322 and part of M13mp19, and carries the gene for the resistance to ampicillin (beta-lactamase), an origin of DNA replication, and a portion of the *E. coli* lac operon with the promoter, operator, and some of the coding region of the lacZ gene (beta-galacto-sidase).

The plasmid pBR322 has been described above, and M13mp19 is a wild type bacteriophage vector suitable for propagation on *E. coli* JM105. Correct ligations for plasmid construction are confirmed by transforming *E. coli* strain JM105, or other suitable host, with the ligation mixture. Successful transformants are selected by ampicillin, tetracycline or other antibiotic resistance, or by using other markers, depending on the mode of plasmid construction, in accordance with methods understood in the art.

In particular, the insertion of the specific DNA fragment of the present invention may be monitored by the loss of beta-galactosidase activity upon transformation of the appropriate host strain. In other words, when the pUC19 plasmid bearing the DNA of interest is introduced into host JM105, the plasmid gives rise to blue colonies on appropriate indicator plates. Cloning DNA fragments into any of the multiple restriction sites inactivates the lac gene, giving rise to white colonies.

In order that those skilled in the art can more fully understand this invention the following examples are set forth. These examples are given solely for purposes of illustration, and should not be considered as expressing limitations unless so set forth in the appended claims. All parts and percentages are by weight unless otherwise stated. Restriction enzymes, ligase, and all commercially available reagents were utilized in accordance with the manufacturer's recommendations. Standard methods and techniques for cloning and molecular analysis, as well as the preparation of standard reagents were performed essentially in accordance with *Molecular Cloning: A Laboratory Manual*, second edition, edited by Sambrook, Fritsch & Maniatis, Cold Spring Harbor Laboratory, 1989).

EXAMPLE 1

Protease Assay

A culture of *Hyphomonas jannaschiana* VP3 (ATCC 33884) was grown in Difco Marine Broth 2216 (MB) (Difco Laboratories, Detroit, Mich.) at 37° C. on an orbital shaker. A comparable culture of *H. jannaschiana* was propagated in AG minimal media (AG), consisting of: aspartic acid, 17 g/l; glutamic acid, 18.8 g/l; serine, 13.4 g/l; artificial sea salt (Instant Ocean, Menasha Corporation, Hartford, Wis.), 23 g/l; biotin, 0.2 µM; 4.6 mM potassium phosphate buffer, pH 7.2. Aliquots of each cell culture were periodically harvested by centrifugation. The harvested cells were resuspended in 0.1M sodium phosphate buffer, pH 7. Cell lysates were prepared by sonication for 2.5 min. In addition, to assaying for the presence of protease activity in the periplasmic space, the outer cell membranes were made permeable by the addition of 0.4 ml toluene per 1 ml of resuspended cells.

Samples of the cell culture supernatants, the toluenized cells, and the cell lysates were each tested for protease activity using an azocasein assay, such as described by Long et al., *J. Gen. Microbiol.* 127:193–199 (1981). One unit of enzyme activity was considered equivalent to an increased absorbance of 0.1 units at a wavelength of 440 nm after a 30 minute incubation at 42° C.

The protease was shown to be an extracellular exoprotease. FIG. 1 is a line graph showing the exoprotease production in *H. jannaschiana* VP3. The lines are identified by the following symbols: o=cell growth as measured by optical density at 550 nm; Δ=extracellular protease activity; and ●=cytoplasmic protease activity. Protease activity was determined by the azocasein assay and expressed as units activity per milliliter of sample (U/ml).

As can be seen in FIG. 1, significant *H. jannaschiana* protease activity was detected in the cell culture supernatant during the early stationary phase and reached a peak after 17 hours. However, no exoprotease activity was detected when cells were propagated in AG minimal medium. Moreover, no protease activity was detected in cell samples which had been sonicated or toluenized. Thus, it was shown that active *H. jannaschiana* protease is not located within either the cytoplasm (sonication) or the periplasmic space (toluenization).

EXAMPLE 2

Induction of Protease Activity

The lack of protease activity which resulted when *H. jannaschiana* were cultured in AG media was correlated with the absence of large peptides in the media to induce enzyme synthesis. *H. jannaschiana* was grown to early stationary phase in AG, and harvested by centrifugation. Subsequently, the stationary phase cells were resuspended at a 10-fold greater cell density in fresh one-tenth volumes of various media selected from: AG minimal medium, AG supplemented with peptone, peptone medium, peptone medium supplemented with yeast extract, or MB. Peptone medium consisted of Difco Peptone, 0.5%; artificial sea salt, 23 g/l; biotin, 0.2 µM; 4.6 mM potassium phosphate buffer, pH 7.2. Where specified, peptone media was supplemented with Difco Yeast Extract at a final concentration of 0.1% (w/v), while AG was supplemented with 0.5% (w/v) Difco Peptone. Each cell culture was maintained at 37° C. and periodically assayed for exoprotease activity during the incubation.

The increased cell density prevented cell growth by nutrient limitation. Thus, the culture was maintained in stationary phase for maximum enzyme production.

Figure 2:
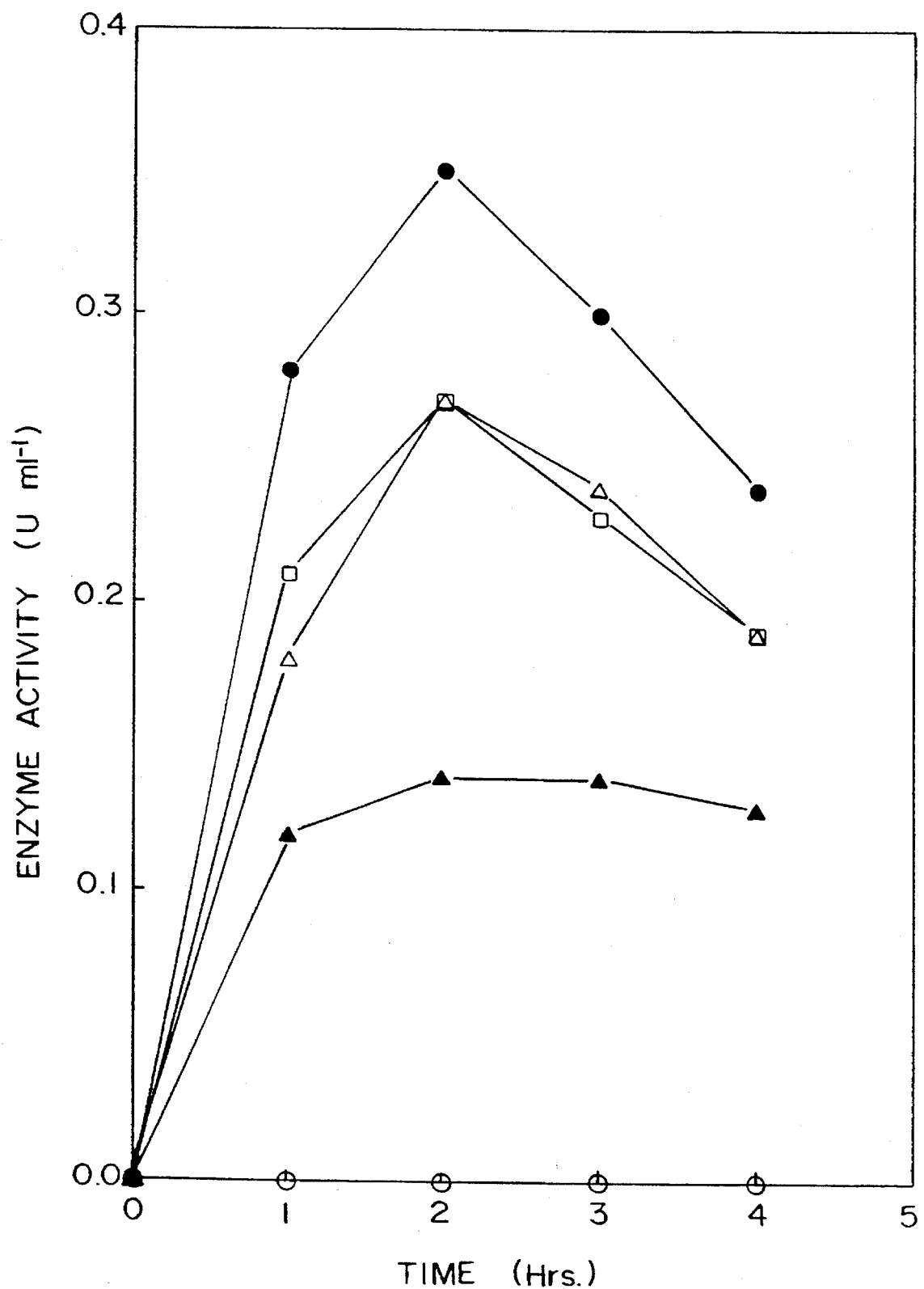
FIG. 2 is a line graph showing the induction of exoprotease activity in *H. jannaschiana* VP3.

The induction of exoprotease activity in *H. jannaschiana* VP3 is shown in FIG. 2. FIG. 2 is a line graph in which the lines are identified by the following specific symbols used to represent the cell culture media: ●=MB; □=peptone media; Δ=peptone media supplemented with yeast extract; ▲=AG supplemented with peptone; and o=AG. Examination of the culture supernatant showed that enzyme induction occurred within one hour after the cells were resuspended in MB. Thus, the induction of *H. jannaschiana* exoprotease production occurred at the onset of stationary phase in the presence of large peptides or protein.

Less efficient exoprotease synthesis occurred in the presence of peptone, while AG supplemented with peptone resulted in a two-fold decrease in exoprotease induction. No protease activity was detected when the cells were cultured in AG. In other words, exoprotease production was essentially absent when *H. jannaschiana* cells were propagated in an amino acid minimal medium, i.e., under conditions in which no large peptides were present.

EXAMPLE 3

Repression of Protease Activity

Since *H. jannaschiana* was shown to preferentially utilize amino acids for growth, the effect of individual amino acids on the activity of extracellular protease was evaluated and the results presented in Table 1. The stationary phase cells were resuspended in a one-tenth volume of MB, then incubated for 30 minutes at 37° C. Exoprotease activity was determined at hourly intervals following introduction of single amino acids at a final concentrations of 0.1% (v/v) o The assay was conducted over a period of 3 hours.

In a similar manner, protease activity was determined following the introduction of 100 mM $(NH_4)_2SO_4$ (ammonium sulfate) or 1% casamino acids to the growth medium.

In the alternative, after allowing protease synthesis and export to proceed for 2.5 hours, the cells were removed by centrifugation, and the supernatant was passed through a 0.22 µm filter. The cell-free protease suspension was then treated, as described above, with single amino acids, casamino acids, or $(NH_4)_2SO_4$. Then, enzyme activity was determined following a 10 minute incubation period.

TABLE 1

| | Repression of protease activity | |
|---|---|---|
| Treatment (%) in free supernatant | Enzyme activity in growth media | Enzyme activity cell |
| control | 100 | 100 |
| alanine | 81 | 56 |
| aspartic acid | 79 | 60 |
| glutamine | 68 | 52 |
| glutamic acid | 86 | 52 |
| glycine | 69 | 82 |
| histidine | 87 | 83 |
| leucine | 61 | 69 |
| proline | 108 | 93 |
| serine | 79 | 64 |
| tryptophan | 71 | 56 |
| casamino acids | 44 | 62 |
| $(NH_4)_2SO_4$ | 56 | 100 |

As shown by the results tabulated in Table 1, exoprotease synthesis by *H. jannaschiana* stationary phase cells was reduced in the presence of casamino acids and most single amino acids. Enzyme activity was also reduced when the extracellular protease found in the cell-free growth media was exposed to either individual amino acids or casamino acids.

Although ammonium sulfate had no affect on extracellular enzyme activity, there was an approximately 50% reduction in the synthesis of the exoprotease (as opposed to complete inhibition). The ammonium sulfate provided a nitrogen source. Therefore, since *H. jannaschiana* has been shown to utilize amino acids as a source of both nitrogen and carbon, the nitrogen limitation modulated the exoprotease synthesis to satisfy the carbon and energy requirements of the bacterium.

EXAMPLE 4

Chemical Inhibition of Protease Activity

The effect of various protease inhibitors on the production of *H. jannaschiana* exoprotease was tested by measuring protease activity following the incubation of the cells with each inhibitor. Stationary phase cells, grown in MB, were pelleted and resuspended in fresh media at one-tenth of the original culture volume. The cell suspension was incubated at 37° C. for 2.5 hours to permit synthesis and export of exoprotease into the culture supernatant. Then the cells were removed by centrifugation and the supernatant was sterilized by filtration through a 0.22 μm filter.

Protease activity was measured after exposure to each inhibitor at 25° C. for 15 minutes. The inhibitors were added at the following final concentrations: 5 mM o-phenanthroline, 60 mM phenylmethyl sulfonamide fluoride (PMSF), 10 mM and 25 mM p-chloromercuribenzoic acid (pCMB), 100 mM EDTA, 80 mM ethylene glycol bis(beta-amino-ethyl-ether)N,N,N',N'-tetraacetic acid (EGTA).

Figure 3:
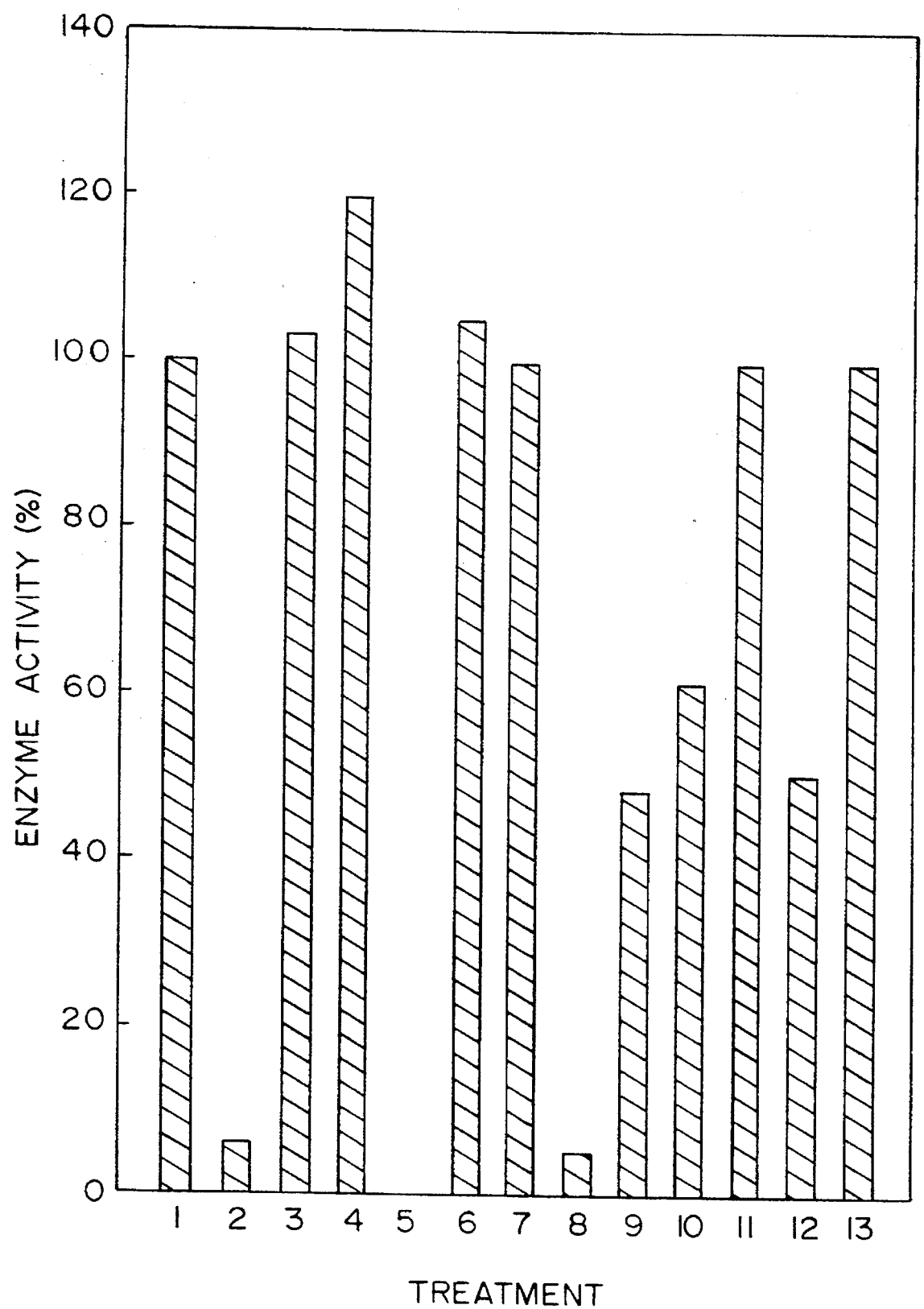
FIG. 3 is a bar graph showing the inhibition of protease activity.

The inhibition of protease activity is shown in FIG. 3 as a bar graph. Each bar represents treatment of the exoprotease with the following: 1=untreated exoprotease; 2=o-phenanthroline; 3=o-phenanthroline and ZnCl; 4=ZnCl; 5=EGTA; 6=EGTA and CaCl; 7=CaCl; 8=EDTA; 9=EDTA and ZnCl; 10=EDTA and CaCl; 11=pCMB (10 mM, final conc.); 12=pCMB (25 mM, final conc.); and 13=PMSF. The enzyme activity was expressed as a percentage of the activity measured in the untreated control.

It was determined that *H. jannaschiana* protease activity was inhibited by o-phenanthroline, EDTA and EGTA (FIG. 3), indicating that *H. jannaschiana* protease is a metalloprotease. Since EDTA concentrations greater than $10^{-2}M$ were necessary to inhibit enzyme activity, the extracellular protease was further classified as an alkaline metalloprotease.

Enzyme activity was unaffected by PMSF and low concentrations of the sulfhydryl reagent pCMB, which are specific inhibitors of serine and cysteine proteases, respectively. However, the activity of *H. jannaschiana* exo-protease was reduced by high concentrations of pCMB (FIG. 3).

In additional assays for which the resulting data are not shown, it was determined that *H. jannaschiana* exoprotease activity was not affected by the thiol protease inhibitor E64. Moreover, enzymatic activity was abolished in the presence of mercaptoethanol, rather than enhanced. Therefore, it was determined that *H. jannaschiana* exoprotease is a metalloprotease which seems to contain a cysteine residue(s) which performs a function other than that of an active site thiol group.

EXAMPLE 5

Recovery of Chemically Inhibited Protease Activity

The ability of the divalent cations $Zn^{2+}$ and $Ca^{2+}$ to restore enzyme activity to inactivated exoprotease was examined by introducing either 5 mM $ZnCl_2$ or 100 mM $CaCl_2$ at a 1:1 molar ratio of ion to inhibitor to the preparations described in Example 4. Following incubation at 25° C. for 15 minutes, protease activity was assayed.

As shown in FIG. 3, *H. jannaschiana* exoprotease which had been inhibited with o-phenanthroline was reactivated by the introduction of $Zn^{2+}$. Since o-phenanthroline is known to specifically form stable complexes with metals belonging to the first transition series, it was determined that the active site of the alkaline metalloprotease was occupied by this metal ion. The finding was consistent with the typical conformation of other bacterial metalloproteases which have been shown to possess one atom of zinc per molecule of enzyme.

By comparison, the EGTA inhibition of *H. jannaschiana* exoprotease activity was reversible by the addition of $Ca^{2+}$, indicating that $Ca^{2+}$ was required in the functional enzyme. Calcium ions have been shown to stabilize zinc-containing metalloproteases and appear to be associated with the ability of the exoprotease to withstand high temperatures.

Both $Zn^{2+}$ and $Ca^{2+}$ partially restored protease activity to enzyme which had been inactivated with EDTA. This observation was surprising since protease activity was totally inhibited following removal of either $Zn^{2+}$ ions with o-phenanthroline or $Ca^{2+}$ ions with EGTA (FIG. 3). However, partial restoration of enzyme activity by either of these divalent cations would result from a titration of bound ion from the EDTA molecule; i.e., the addition of excess $Ca^{2+}$ released bound $Zn^{2+}$ and vice versa. Moreover, it was of particular interest that additional $Zn^{2+}$ ions significantly increased the activity of the native protease, while additional $Ca^{2+}$ ions had no detectable effect on protease activity (FIG. 3).

EXAMPLE 6

Thermal Stability of *H. jannaschiana* Exoprotease

Filtered supernatant containing *Hyphomonas jannaschiana* exoprotease was maintained at 75° C. and 100° C. for various periods of time. Then, the enzyme was allowed to recalibrate to 25° C., and subsequently assayed for protease activity using the azocasein assay.

Over 60% of the enzyme activity remained following incubation of the filtered stationary phase culture supernatant at 75° C. for 30 minutes. Moreover, treatment of the preparation at 100° C. (boiling) for 5 minutes failed to destroy the extracellular protease activity, but reduced it by only 41%. Therefore, alkaline exoprotease produced by *H. jannaschiana* was shown to be unexpectedly stable and active at high temperatures.

EXAMPLE 7

Polyacrylamide Gel Electrophoresis and Assay of Exoprotease Activity

The extracellular proteins produced by *Hyphomonas jannaschiana* were electrophoretically separated in 8% polyacrylamide gels containing 2% SDS and as a copolymerized substrate, 1% gelatin. Filtered protease samples from the media supernatant of stationary phase cultures were treated with 2.5% (w/v) SDS and 2% (w/v) glycerol at 37° C. for 30 minutes. Electrophoresis was performed at 15 mA for 2 hours at 4° C. in a slab gel electrophoresis unit (Hoefer SE250-Mighty Small II, San Francisco, Calif.). The SDS was removed by washing the gel with Triton X-100 containing 10 mM $CaCl_2$ for 30 minutes at 25° C. Then the gel was immersed in 0.1M glycine buffer, pH 9, containing 10 mM $CaCl_2$ and incubated at 37° C. for 2 hours. The electrophoresed gels were assayed for protease activity by gelatin hydrolysis, such as described by Hare et al., *J. Gen. Microbiol.* 129:1141–1147 (1983). The gels were stained with amido black to visualize proteolysis of the gelatin by negative staining.

Figure 4:
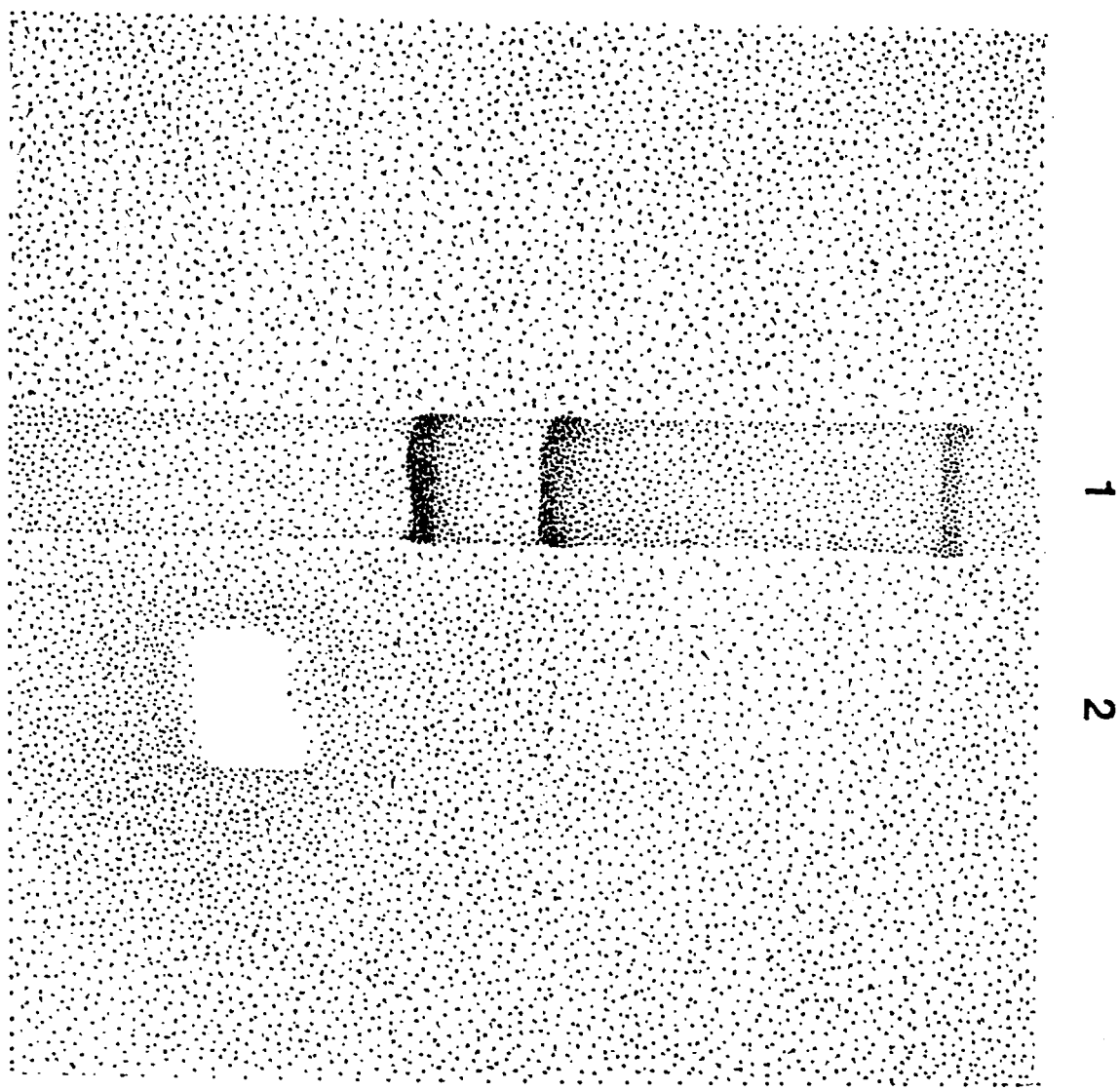
FIG. 4 is a photograph showing the electrophoretic analysis of exoprotease activity in *H. jannaschiana* VP3.

Separation of the proteins present in the stationary phase culture supernatant by SDS polyacrylamide gel electrophoresis, followed by the removal of SDS and subsequent digestion of gelatin incorporated in the acrylamide matrix, resulted in the identification of a single, major band of proteolysis after negative-staining with amido black. FIG. 4 is an autoradiograph showing the electrophoretic analysis of exoprotease activity in *H. jannaschiana* VP3 in which the lanes were identified as follows: Lane 1, molecular weight standards: myosin (200,000), *E. coli* beta-galactosidase (116,300), rabbit muscle phosphorylase b (97,400), bovine serum albumin (66,200); lane 2, filtered media supernatant of a stationary phase culture of *H. jannaschiana*. As shown in FIG. 4, the approximate molecular weight of the *H. jannaschiana* exoprotease was determined to be 86,000 daltons.

EXAMPLE 8

Inhibition of Protease Export

Since protease activity was not discernable in the cytoplasmic fraction of the *H. jannaschiana* stationary phase cells, it appeared that the protease was initially synthesized as an inactive proenzyme which was then processed to the active form during export. Thus, protease export was examined in the presence of quinacrine, a signal peptidase inhibitor. Protease export in the presence of quinacrine was examined using two approaches. An actively growing culture of *H. jannaschiana* was monitored with respect to both optical density at 550 nm and extracellular enzyme activity in the presence of 0.025 mM quinacrine. In order to eliminate the effect of quinacrine on *H. jannaschiana* growth, cells were initially propagated to stationary phase, and subsequently maintained in the non-proliferating state by 10-fold concentration in fresh media which was supplemented with 0.025 mM quinacrine.

TABLE 2

| Inhibition of protease export by quinacrine | |
|---|---|
| Time (min) | Enzyme activity |
| 30 | 100[a] |
| 40 | 33 |
| 60 | 50 |
| 90 | 78 |
| 120 | 82 |
| 180 | 90 |

[a]Protease activity expressed as a fraction of that measured in an untreated control.

The cells exhibited a 67% reduction in exported enzyme 40 minutes after the addition of quinacrine (Table 2). Subsequently, extracellular protease activity returned to that of the untreated control after an additional 140 minutes of incubation. Quinacrine had no affect on functional extracellular protease activity.

Both growth rate and extracellular enzyme activity were transiently reduced in the presence of 0.025 mM quinacrine. Seven hours after treatment, the optical density of the culture was reduced by 48%, and exoprotease activity was diminished by 73%, as compared to that of untreated cells. Subsequently, both cell density and exoprotease activity returned to normal levels following an additional 6 hour growth period.

Thus, it was shown that the inducible alkaline metalloprotease synthesized by *H. jannaschiana* ($MW_{approx}$ 80,000) was exported from the cell via a signal peptidase. The export involves a mechanism whereby an inactive, cytoplasmic proenzyme was processed by a signal peptidase into functional extracellular protease.

EXAMPLE 9

Determination of the Nucleotide Sequence of the *Hyphomonas jannaschiana* Gene for Alkaline Metalloprotease A synthetic oligonucleotide-directed strategy for double-stranded sequencing was utilized to determine the nucleotide sequence of *Hyphomonas jannaschiana* alkaline metalloprotease. Two oligonucleotides which were complementary to the vector sequences on both ends of the protease sequence and which had the following sequence:

PI: 5' CGAGATCTGTCGTATCGT 3'

PII: 5' TCCGAGATCCGAATACAT 3' were synthesized using phosphoramidite chemistry on a Milligen 7500 DNA synthesizer (Millipore Corp., Bedford, Mass.). The double stranded template was alkaline denatured by addition of Denaturation solution (0.2N NaOH, 0.2 mM EDTA), followed by neutralization with Neutralization solution (500 mM Tris-HCl, pH 4.5). 0.3M Sodium acetate was added, and the template was ethanol precipitated. The primer was added to the denatured template, the mixture was boiled at 100° C., then placed at 37° C. Sequencing reactions with Sequenase Version 2 and $\alpha$-($^{35}$S)dATP were conducted as prescribed by U.S. Biochemical Corp. (Cleveland, Ohio). The completed reactions were run on 6% denaturing polyacrylamide gels (6% acrylamide, 7M urea, 1X TBE) and autoradiographed. Sequencing data showed that the insert was 190 bp long and was "in frame" with the Tet gene in *E. coli* pBR322. It was determined that there was a site which was very close to the conserved active site of the metalloprotease.

EXAMPLE 10

Preparation of Plasmid pJS1

*E. coli* JM105 host cells were transformed by the insertion of either pBR322 or pUC19 vectors containing at least a portion of the DNA fragment encoding the thermostable alkaline metalloprotease. Over 7000 clones were produced, from which a number of positive clones were identified by ampicillin resistance on milk plates. The protease clones hybridized strongly with *H. jannaschiana* chromosomal DNA. However, the selected clones did not demonstrate protease activity while growing in liquid media.

Clone pJS1 was selected from among the positive protease clones. Restriction mapping indicated that the clone contained an insert of about 300 bp in plasmid pBR322. The plasmid was isolated and named recombinant plasmid pJS1.

EXAMPLE 11

Screening of the *Hyphomonas jannachiana* Gene Bank

A specific hybridization probe which is complementary to the protease fragment in the plasmid pJS1 was synthesized via Polymerase Chain Reaction (PCR). PCR reaction mixtures consisted of 10 ng of the appropriate plasmid (pJS1), 100 ng of each primer, 1X Taq DNA polymerase buffer (25 mM Tris-Cl, pH8.3; 50 mM NaCl; 5 mM $MgCl_2$; 200 μM each of dATP, dCTP, dGTP, dTTP, and 0.5 U Taq DNA Polymerase (Promega Biotech, Madison, Wis.), in $H_2O$ to a volume of 100 μl. The PCR reactions were incubated in a Perkin-Elmer Cetus DNA Thermal Cycler and performed with a 1 minute denaturation period at 94° C., 2 minute annealing period at 50° C., and 3 minute extension period at 72° C. This was conducted for 30 reaction cycles, followed by a final 7 minute extension period at 72° C.

Aliquots of the completed reaction were electrophoresed on a 1.5% agarose gel and to confirmed the presence of the predicted 200 bp protease fragment. The 200 bp band was excised from the agarose gel and the DNA was recovered by utilizing a Mermaid kit (Bio 101, Inc., La Jolla, Calif.). The recovered DNA was phenol/chloroform extracted, chloroform extracted, and ethanol precipitated.

The DNA was labeled by random primed incorporation of digoxygenin-labeled deoxyuridine-triphosphate (Boehringer-Mannheim Corp., Indianapolis, Ind.). The reaction mixture consisted of 1 μg of freshly denatured DNA, 2 μl hexanucleotide mixture, 2 μl dNTP labeling mixture (containing dCTP, dGTP, dATP, dTTP and dig-dUTP), 0.5 U Klenow enzyme, and H20 to a final volume of 20 μl. The reaction mixture was incubated for 3 hours at 37° C. Then the labeling reaction was stopped by the addition of an EDTA solution (0.2 moles/l, pH 8.0). The labeled DNA was precipitated with LiCl (4 moles/l) and ethanol.

Although the present invention has been described with reference to the presently preferred embodiments, the skilled artisan will appreciate that various modifications, substitutions, omissions, and changes may be made without departing from the spirit of the invention. Accordingly, it is intended that the scope of the present invention be limited only by the scope of the following claims, including equivalents thereof.

---

What is claimed is:

1. A native purified thermostable alkaline metalloprotease of *Hyphomoms jannaschiana* having the following properties:
   a) an optimal activity at a pH of approximately 9.5 at a reaction temperature of about 60° to 65° C.;
   b) lack of inhibition by 60 mM phenylmethyl sulfonamide fluoride (PMSF); and
   c) a molecular weight of approximately 80,000 daltons.

2. The purified thermostable alkaline metalloprotease of claim 1, which is produced by a microorganism *Hyphomonas jannaschiana* and which exhibits enzymatic activity in an azocasein assay.

3. The purified thermostable alkaline metalloprotease of claim 2, which is produced by *Hyphomonas jannaschiana* VP3 (ATCC 33884).

4. The purified thermostable alkaline metalloprotease of claim 2, comprising the amino acid sequence (SEQ ID NO:2):

```
Glu Ile Cys Arg Ile Val Met Asp Gly His Cys Glu Lys Gln
 1               5                  10
Gly Asp Ala Glu Cys His Asp Asp Gln Gln Ser Ala Arg Pro
15                  20                  25
Ala Asp Gln Arg Ile Asn Gln Asp Val Glu Gln Val Asp Asp
        30              35                  40
Gln Phe Glu Glu Gln Gly Pro Gly Arg Asn Val Cys Gly Ile
        45              50                  55
Asn Val Phe Gly Ser
            60
```
or an allelic variant thereof.

5. A biologically pure culture of *Hyphomonas jannaschiana* VP3 which synthesizes the thermostable alkaline metalloprotease of claim 1.

6. The process for the production of the thermostable alkaline metalloprotease of claim 1, wherein said process comprises:
   a) culturing the alkaline protease producing bacterium in a nutrient fermentation medium;
   b) maintaining the bacterium at stationary growth phase for a period of time which is sufficient for protease to be exported into said fermentation medium;
   c) separating bacterium from cell-modified fermentation medium; and
   d) isolating and recovering said alkaline protease from said cell-modified fermentation medium.

7. The process of claim 6, wherein the thermostable alkaline metalloprotease producing bacterium is *Hyphomonas jannaschiana*.

8. The process of claim 6, wherein the pH of the nutrient medium is in the range of about 7.0 to about 8.5.

9. The process of claim 6, wherein the bacterium is maintained at temperature in the range of from about 30° C. to about 37° C.

10. An isolated DNA sequence which codes for the thermostable alkaline metalloprotease of claim 2.

11. The nucleotide sequence of claim 10, comprising the sequence (SEQ ID NO: 1):

GATCC GAG ATC TGT CGT ATC GTA ATG GAC GGC CAT TGC GAG AAA CAG GGC GAT GCT GAG TGC CAC GAC GAC CAG CAG TCC GCT CGT CCG GCG GAT CAG CGG ATA AAT CAG GAT GTA GAA CAG GTT GAT GAC CAG TTC GAA GAA CAG GGT CCA GGC CGG AAC GTT TGC GGC ATA AAT GTA TTC GGA TCT CG.

12. An isolated DNA fragment comprising a DNA sequence which encodes an active, functional thermostable alkaline metalloprotease wherein said metalloprotease is endogenous to *Hyphomonas jannaschiana* and exhibits enzymatic activity in an azocasein assay, said DNA fragment being positioned in operable linkage with regulatory DNA sequence elements compatible with a host transformed with said DNA fragment and promoting the expression of said metalloprotease.

13. A purified thermostable alkaline metalloprotease produced by expression of the DNA of claim 12.

14. The isolated DNA fragment of claim 12, which encodes an active, functional thermostable alkaline metalloprotease wherein said metalloprotease is endogenous to *Hyphomonas jannaschiana* VP3 (ATCC 33884) and exhibits enzymatic activity in an azocasein assay, said DNA being positioned in operable linkage with regulatory DNA sequence elements compatible with a host transformed with said DNA fragment and promoting the expression of said metalloprotease.

15. The purified thermostable alkaline metalloprotease of claim 4, wherein said metalloprotease is recombinantly produced.

16. A gram negative microorganism transformed with the isolated DNA fragment of claim 10, wherein said microorganism expresses an active, functional thermostable alkaline metalloprotease wherein said metalloprotease is endogenous to *Hyphomonas jannaschiana* and exhibits enzymatic activity in an azocasein assay, said DNA being positioned in operable linkage with regulatory DNA sequence elements compatible a host transformed with said DNA fragment and promoting the expression of said metalloprotease.

17. A genetic library comprising fragments of the genomic DNA of the culture of *Hyphomonas jannaschiana* VP3 of claim 5.

18. An isolated DNA fragment comprising at least a portion of the isolated DNA fragment of claim 10, which when expressed is sufficient to translate into an active, functional thermostable alkaline metalloprotease which is capable of exhibiting enzymatic activity in an azocasein assay.

19. A plasmid capable of stable maintenance in a bacterial host, comprising at least a portion of the isolated DNA fragment of claim 11, which when expressed is sufficient to translate into an active, functional thermostable alkaline metalloprotease which is capable of exhibiting enzymatic activity in an azocasein assay.

20. A plasmid according to claim 19, wherein said plasmid is pJS1.

21. A bacterial host containing at least a portion of the isolated DNA fragment of claim 11, which when expressed is sufficient to translate into an active, functional thermostable alkaline metalloprotease which is capable of exhibiting enzymatic activity in an azocasein assay.

22. The protein expressed by the bacterial host of claim 21.

23. The protein expressed by the bacterial host of claim 21, wherein the C-terminus of said sequence is attached to the lacZ alpha peptide encoded by a portion of pUC19.

24. The bacterial host according to claim 21, wherein said bacterial host is a gram-negative bacterium.

25. The bacterial host according to claim 24, wherein said bacterial host is *E. coli*.

26. An *E. coli* comprising the plasmid according to claim 19.

27. An *E. coli* comprising the plasmid according to claim 20.

28. A process for the production of the thermostable alkaline metalloprotease of claim 1, which comprises a) transforming host cells with an isolated DNA fragment comprising a DNA sequence which encodes the metalloprotease wherein said metalloprotease is endogenous to *Hyphomonas jannaschiana* and exhibits enzymatic activity in an azocasein assay, said DNA fragment being positioned in operable linkage with regulatory DNA sequence elements compatible a host transformed with said DNA fragment and promoting the expression of said metalloprotease;

b) culturing said transformant, thereby allowing the production of said protease;

c) confirming the transformation by screening for expression of the enzymatic activity; and d) recovering said protease from said culture.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 190 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GATCCGAGAT  CTGTCGTATC  GTAATGGACG  GCCATTGCGA  GAAACAGGGC  GATGCTGAGT    60

GCCACGACGA  CCAGCAGTCC  GCTCGTCCGG  CGGATCAGCG  GATAAATCAG  GATGTAGAAC   120

AGGTTGATGA  CCAGTTCGAA  GAACAGGGTC  CAGGCCGGAA  CGTTTGCGGC  ATAAATGTAT   180

TCGGACTCCG                                                              190
```

( 2 ) INFORMATION FOR SEQ ID NO:2:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: protein (xi) SEQUENCE DESCRIPTION: SEQ ID NO:2:

```
Glu Ile Cys Arg Ile Val Met Asp Gly His Cys Glu Lys Gln Gly Asp
 1               5                  10                  15
Ala Glu Cys His Asp Asp Gln Gln Ser Ala Arg Pro Ala Asp Gln Arg
            20                  25                  30
Ile Asn Gln Asp Val Glu Gln Val Asp Asp Gln Phe Glu Glu Gln Gly
        35                  40                  45
Pro Gly Arg Asn Val Cys Gly Ile Asn Val Phe Gly Ser
    50                  55                  60
```